United States Patent
Davidsen et al.

(10) Patent No.: US 10,178,986 B2
(45) Date of Patent: *Jan. 15, 2019

(54) ULTRASONIC MATRIX ARRAY PROBE WITH THERMALLY DISSIPATING CABLE AND BACKING BLOCK HEAT EXCHANGE

(71) Applicant: KONINKLIJKE PHILIPS N.V., Eindhoven (NL)

(72) Inventors: Richard Edward Davidsen, Eindhoven (NL); Michael Scarsella, Eindhoven (NL); James Christopher Taylor, Eindhoven (NL); Andrew Lee Robinson, Eindhoven (NL); Wojtek Sudol, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/862,894

(22) Filed: Jan. 5, 2018

(65) Prior Publication Data

US 2018/0125463 A1 May 10, 2018

Related U.S. Application Data

(63) Continuation of application No. 14/385,783, filed as application No. PCT/IB2013/051639 on Mar. 1, 2013, now Pat. No. 9,872,669.

(Continued)

(51) Int. Cl.
*A61B 8/00* (2006.01)
*G10K 11/00* (2006.01)
(Continued)

(52) U.S. Cl.
CPC .......... *A61B 8/546* (2013.01); *A61B 8/4444* (2013.01); *A61B 8/4483* (2013.01);
(Continued)

(58) Field of Classification Search
CPC ..... A61B 8/546; A61B 8/4488; A61B 8/4444; A61B 8/4483; A61B 8/4494;
(Continued)

(56) References Cited

U.S. PATENT DOCUMENTS 5,213,103 A 5/1993 Martin
5,560,362 A 10/1996 Sliwa et al.
(Continued)

FOREIGN PATENT DOCUMENTS

DE 103502183 5/2005
EP 0782125 A2 7/1997
(Continued)

*Primary Examiner* — Angela M Hoffa

(57) ABSTRACT

A matrix array probe including a transducer array and integrated circuitry coupled to the transducer elements dissipates heat generated by the array and integrated circuitry through the cover of the transducer probe. A pump in the probe connector pumps fluid through a closed loop system including inbound an outbound fluid conduits in the cable. The fluid conduits in the cable are separated by the cable electrical conductors for the probe. The heat transfer in the probe is done by a heat exchanger in the transducer backing block. Additional cooling may be provided by metal to metal contact with a chiller in the ultrasound system.

15 Claims, 6 Drawing Sheets

Related U.S. Application Data

(60) Provisional application No. 61/613,114, filed on Mar. 20, 2012.

(51) Int. Cl.
  *G01S 7/52* (2006.01)
  *A61B 18/00* (2006.01)
  *G01S 15/89* (2006.01)

(52) U.S. Cl.
  CPC .......... *A61B 8/4488* (2013.01); *G10K 11/004* (2013.01); *A61B 8/4494* (2013.01); *A61B 2018/00023* (2013.01); *G01S 7/52079* (2013.01); *G01S 15/8915* (2013.01)

(58) Field of Classification Search
  CPC ........ A61B 2018/00023; G10K 11/004; G01S 7/52079; G01S 15/8915
  See application file for complete search history.

(56) References Cited

U.S. PATENT DOCUMENTS

| | | |
|---|---|---|
| 5,648,941 A | 7/1997 | King |
| 5,721,463 A | 2/1998 | Snyder |
| 6,585,692 B1 | 7/2003 | Worthen |
| 6,589,271 B1 | 7/2003 | Tzeng |
| 6,673,328 B1 | 1/2004 | Klett |
| 6,942,644 B2 | 9/2005 | Worthen |
| 7,314,447 B2 | 1/2008 | Park |
| 7,909,817 B2 | 3/2011 | Griffin |
| 8,273,025 B2 | 9/2012 | Shikata |
| 8,409,101 B2 | 4/2013 | Hongou |
| 8,529,561 B2 | 9/2013 | Griffin |
| 9,237,880 B2 | 1/2016 | Davidsen |
| 9,867,592 B2 * | 1/2018 | Davidson .............. A61B 8/4444 |
| 9,872,669 B2 * | 1/2018 | Davidsen ................ A61B 8/546 |
| 2003/0029010 A1 | 2/2003 | Aime |
| 2003/0195465 A1 | 10/2003 | Worthen |
| 2004/0100163 A1 | 5/2004 | Baumgartner et al. |
| 2005/0075573 A1 | 4/2005 | Park |
| 2006/0043839 A1 | 3/2006 | Wildes et al. |
| 2006/0173344 A1 | 8/2006 | Marian |
| 2006/0186765 A1 | 8/2006 | Hashimoto |
| 2006/0261707 A1 | 11/2006 | Wildes et al. |
| 2006/0282068 A1 | 12/2006 | Griffin |
| 2007/0167826 A1 | 7/2007 | Lee |
| 2008/0077017 A1 | 3/2008 | Hyuga |
| 2008/0098816 A1 | 5/2008 | Yamashita et al. |
| 2008/0243001 A1 | 10/2008 | Oakley |
| 2008/0315724 A1 | 12/2008 | Kunkel |
| 2010/0331702 A1 | 12/2010 | Hongou |
| 2011/0230872 A1 | 9/2011 | Griffin |
| 2011/0282211 A1 | 11/2011 | Shikata |
| 2012/0238880 A1 | 9/2012 | Davidsen |
| 2013/0090650 A1 | 4/2013 | Jenson |
| 2013/0114379 A1 | 5/2013 | Fischer |
| 2013/0345567 A1 | 12/2013 | Sudol |
| 2014/0058270 A1 | 2/2014 | Davisdon |
| 2014/0074072 A1 | 3/2014 | Griffin |
| 2015/0045670 A1 | 2/2015 | Davidson |
| 2015/0099978 A1 * | 4/2015 | Davidsen ............. A61B 8/4483 600/459 |
| 2015/0272669 A1 | 10/2015 | Brucker |

FOREIGN PATENT DOCUMENTS

| | | |
|---|---|---|
| JP | 2007282743 A | 11/2007 |
| WO | 2008121238 A2 | 9/2008 |
| WO | 2012123906 A2 | 9/2012 |

* cited by examiner

ULTRASONIC MATRIX ARRAY PROBE WITH THERMALLY DISSIPATING CABLE AND BACKING BLOCK HEAT EXCHANGE

The present application is a continuation of U.S. patent application Ser. No. 14/385,783 filed Sep. 17, 2014, which is the U.S. National Phase application under 35 U.S.C. § 371 of International Application No. PCT/IB2013/051639, filed Mar. 1, 2013, which claims the benefit of U.S. Provisional Application Ser. No. 61/613,114 filed Mar. 20, 2012. These applications are hereby incorporated by reference herein.

This invention relates to medical diagnostic ultrasound systems and, in particular, to ultrasonic matrix array probes which dissipate heat generated by the probe ASIC through the probe cable.

Two dimensional array transducers are used in ultrasonic imaging to scan in three dimensions. Two dimensional arrays have numerous rows and columns of transducer elements in both the azimuth and elevation directions, which would require a large number of cable conductors to couple signals between the probe and the mainframe ultrasound system. A preferred technique for minimizing the number of signal conductors in the probe cable is to perform at least some of the beamforming in the probe in a microbeamformer ASIC (application specific integrated circuit.) This technique requires only a relatively few number of partially beamformed signals to be coupled to the mainframe ultrasound system, thereby reducing the required number of signal conductors in the cable. However a large number of signal connections must be made between the two dimensional array and the microbeamformer ASIC. An efficient way to make these connections is to design the transducer array and the ASIC to have flip-chip interconnections, whereby conductive pads of the transducer array are bump bonded directly to corresponding conductive pads of the ASIC.

The high density electronic circuitry of the microbeamformer ASIC can, however, produce a significant amount of heat in its small IC package, which must be dissipated. There are two main directions in which this heat can flow. One direction is forward through the acoustic stack toward the lens at the patient-contacting end of the probe. This forward path exhibits relatively low resistance to thermal flow. Build-up of heat in the lens must then be prevented by reducing transmission voltage and/or the pulse repetition frequency, which adversely affects probe performance.

The preferred thermal conduction direction is to the rear, away from the lens and patient and toward a heat spreader (typically aluminum) at the rear of the probe. But generally located behind the transducer stack, the array elements and the microbeamformer ASIC, is an acoustic backing block. The purpose of the acoustic backing block is to attenuate ultrasonic energy emanating from the rear of the acoustic stack and prevent this energy from causing reverberations that are reflected toward the acoustic stack. An acoustic backing block is generally made of a material with good acoustic attenuation properties such as an epoxy loaded with micro-balloons or other sound-deadening particles. Such materials, however, typically have poor thermal conductivity. Hence it is desirable to provide an acoustic backing block for an ultrasound probe which exhibits good acoustic attenuation of acoustic energy entering the block, good thermal conductivity toward the rear of the probe and away from the lens, good mechanical structure which can support the acoustic stack as needed, and appropriate electrical isolation of the microbeamformer ASIC from other conductive components of the probe.

An acoustic backing block which exhibits these characteristics is described in U.S. patent application Ser. No. 61/453,690, filed Mar. 17, 2011. The backing block described in this patent application is formed of a matrix of a highly thermally conductive material with internal acoustic damping members. A preferred material for the thermally conductive material is graphite exhibiting a high thermal conductivity. The graphite is formed into a rigid block with the mechanical stability to support a transducer array stack. The internal acoustic damping members, which can be formed by drilling holes in the graphite block which are filled with acoustic damping material, are preferably located such that an acoustic wave traveling normal to the rear surface of the transducer array stack must encounter an acoustic damping member and be acoustically attenuated.

While this thermally conductive backing block is an excellent conductor of heat away from the microbeamformer ASIC, there remains a problem in how and where to dissipate the heat. Without more, the heat must dissipate from the probe itself. Ultrasound transducers with no internal electronics can effectively dissipate heat from the transducer elements using modest thermal measures such as metal heat fins in the backing, the probe frame, and heat sinks in the probe. As integrated circuitry has begun to be located in the probe, passive cooling elements such as heat spreaders internal to and coupled to the probe housing have been used to dissipate the additional heat. See, e.g., U.S. patent application Ser. No. 61/486,796, filed May 17, 2011. However, even such improved passive cooling is unable to fully dissipate all the heat generated by the integrated circuitry, leading to compromises in performance such as those mentioned above to stay below thermal limits. What is needed is additional capacity to dissipate transducer heat. One further approach beyond the probe itself is to connect the thermal path in the probe to metal components in the cable (i.e., the signal/power conductors and the shield braid) to dissipate heat through these components. However, the present inventors have found that this does not significantly improve the heat dissipation capability because of limitations in the thermal conductivity along the cable in the conductors and braid, and the thermal conductivity from the conductors and braid to the cable surface, where the heat is dissipated. The present invention is directed to more effectively use the transducer cable to help dissipate this additional heat. This can help manage both lens face temperature and probe handle temperature.

In accordance with the principles of the present invention, an ultrasonic matrix array probe is described which dissipates heat generated by the probe microbeamformer ASIC through the probe cable by means of a fluid based closed loop active cooling system. A heat exchanger in the probe is in thermal communication with a thermally conductive backing block thermally coupled to the probe ASICs. In one embodiment the heat exchanger is embedded in the thermally conductive backing block. A fluid is pumped through fluid conduits in the cable and through the probe heat exchanger by a pump located in the probe case or the probe connector at the proximal end of the cable. The fluid conduits are formed and arranged in the cable in a manner which efficiently conducts heat from the fluid to the cable surface where it is dissipated by radiation and convection. Additional cooling can be provided by metal-to-metal contact between the probe connector and the ultrasound system which provides additional cooling capacity without a fluid connection between the ultrasound system and the closed loop system of the probe. The closed loop cooling system is completely contained within the probe, its cable, and probe connector.

Figure 1:
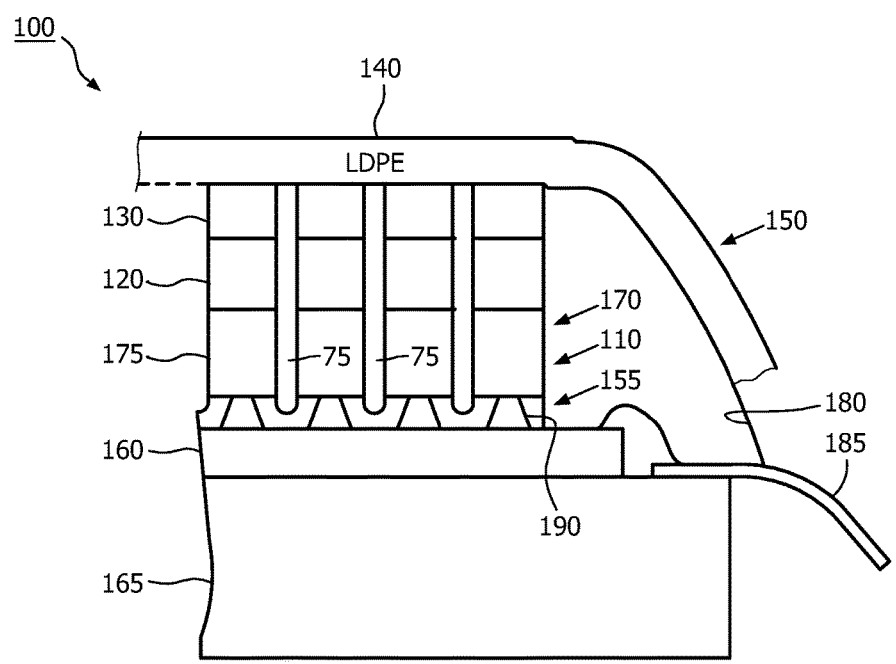
FIG. 1 illustrates a matrix array probe acoustic stack with a thermally conductive backing block constructed in accordance with the principles of the present invention.

Referring first to FIG. 1, an acoustic stack 100 with a thermally conductive backing block which is constructed in accordance with the principles of the present invention is shown schematically. A piezoelectric layer 110 such as PZT and two matching layers 120, 130 bonded to the piezoelectric layer are diced by dicing cuts 75 to form an array 170 of individual transducer elements 175, four of which are seen in FIG. 1. The transducer array 170 may comprise a single row of transducer elements (a 1-D array) or is a piezoelectric plate diced in two orthogonal directions to form a two-dimensional (2D) matrix array of transducer elements. The matrix array 170 may also comprise a one or two dimensional array of micromachined ultrasound transducer (MUTs) formed on a semiconductor substrate by semiconductor processing. The matching layers match the acoustic impedance of the piezoelectric material to that of the body being diagnosed, generally in steps of progressive matching layers. In this example the first matching layer 120 is formed as an electrically conductive graphite composite and the second matching layer 130 is formed of a polymer loaded with electrically conductive particles. A ground plane 180 is bonded to the top of the second matching layer, and is formed as a conductive layer on a film 150 of low density polyethylene (LDPE) 140. The ground plane is electrically coupled to the transducer elements through the electrically conductive matching layers and is connected to a ground conductor of flex circuit 185. The LDPE film 150 forms the third and final matching layer 140 of the stack.

Below the transducer elements is an integrated circuit 160, an ASIC, which provides transmit signals for the transducer elements 175 and receives and processes signals from the elements. Conductive pads on the upper surface of the integrated circuit 160 are electrically coupled to conductive pads on the bottoms of the transducer elements by stud bumps 190, which may be formed of solder or conductive epoxy. Signals are provided to and from the integrated circuit 160 by connections to the flex circuit 185. Below the integrated circuit 160 is a backing block 165 which attenuates acoustic energy emanating from the bottom of the transducer stack. In accordance with the principles of the present invention, the backing block also conducts heat generated by the integrated circuit away from the integrated circuit and the transducer stack and away from the patient-contacting end of the transducer probe.

Figure 2:
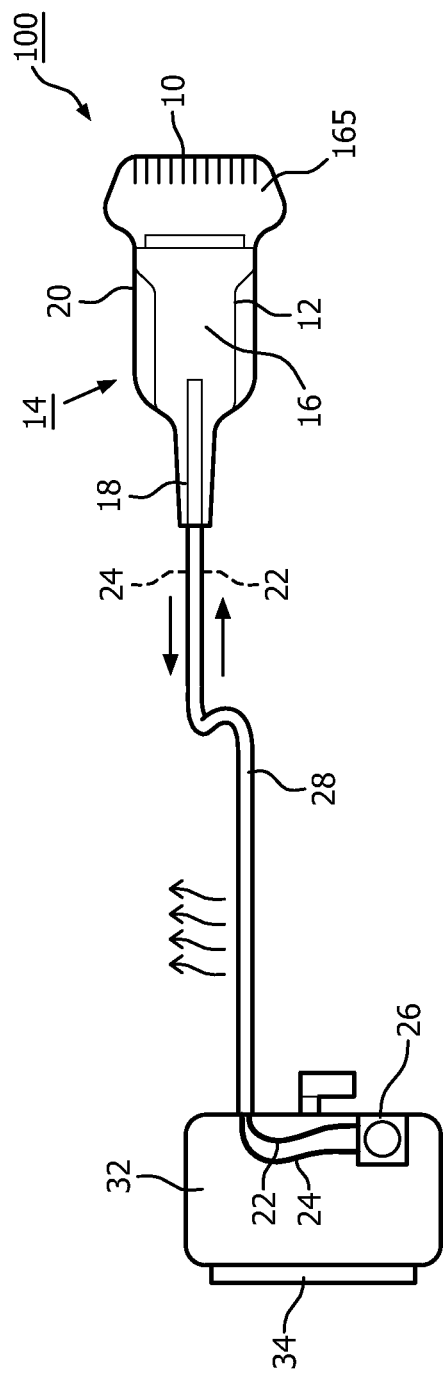
FIG. 2 illustrates a matrix array probe, connector and thermally dissipating cable constructed in accordance with the principles of the present invention.

FIG. 2 illustrates a matrix array transducer probe 14, cable 28 and connector 32 constructed in accordance with the principles of the present invention. The probe components are housed in an external polymeric case 20. A strain relief sleeve 18 surrounds the cable 28 where it enters the probe case 20. A structure 12 inside the case called a "spaceframe" supports the internal components of the probe and fits to the internal dimensions of the case. At the distal, patient-contacting end of the probe is the matrix array acoustic stack 100. The non-conductive patient-contacting surface of the probe through which ultrasound waves are sent and received is referred to as a lens 10. Behind the two dimensional transducer array 170 are the beamformer ASICs 160 and behind the ASICs and in thermal contact with them is the acoustically attenuating and thermally conductive backing block 165. In accordance with the present invention, a heat exchanger 16 is in thermal contact with the back of the thermally conductive backing block 165. Cooling fluid is pumped into an inlet port of the heat exchanger through a first conduit 22 and warmed fluid carrying heat from the probe flows out of the probe through a second conduit 24. These conduits pass through the probe cable 28 along with the signal and power conductors for the probe 14. The heat conveyed by the fluid in the second conduit 24 dissipates through the external covering of the cable as described more fully below. The fluid in this closed loop system is continuously circulated by a pump 26 which is coupled to the two fluid conduits 22 and 24. The pump is located in the probe connector 32 which connects the probe and its cable to a mainframe ultrasound system. An electrical socket 34 in the connector mates with a plug on the ultrasound system when the connector 32 is attached to the ultrasound system. In this arrangement a cooling fluid is pumped through the cable conduit 22 and through the heat exchanger 16, where it picks up heat from the ASICs 160 which has been conducted away from the ASICs by the thermally conductive backing block. The warmed fluid exits the probe 14 through the conduit 24 and passes through the cable 28, where it dissipates heat by convection and conduction through the surface of the cable. Since probe cables are quite long, there is a considerable length of cable and cable surface area from which to dissipate the heat picked up in the probe. The flowing fluid returns in a cooled state to the pump 26 and the process continues.

Figure 3:
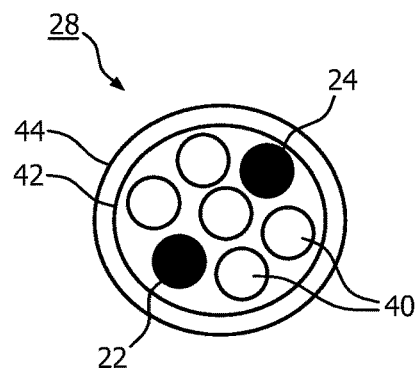
FIGS. 3, 4, 5 and 6 illustrate different bundling of transducer conductors and fluid conduits for probe heat dissipation in a probe cable in accordance with the principles of the present invention.

FIGS. 3-6 illustrate a number of techniques for configuring a fluid-based, thermally dissipating probe cable 28 for efficient and effective heat transfer and dissipation from the warmed fluid. In the implementation of FIG. 3 the outbound (from the probe; heated) conduit 24 is located on one side of the cable and the inbound (cool) conduit 22 is located on the other side of the cable, separated by the signal and power electrical conductors running from the connector 32 to the probe 14. In this implementation the electrical conductors are bundled into discrete sub-bundles 40. By keeping the electrical conductors into sub-bundles the conductor sub-bundles will stay in place around and between the fluid conduits and will not separate individually and be displaced as can happen with individual unbundled conductors. The sub-bundles of electrical conductors will thus keep the fluid conduits separated from each other thermally on opposite sides of the cable. The sub-bundles and conduits are surrounded by a metallic and/or graphite cable braid 42 which provides an r.f. electrical shield for the electrical conductors and also runs the length of the cable. The cable braid also provides efficient heat transfer from the outbound (warm) conduit 24 to the outer cable jacket. Heat from the fluid in the outbound conduit 24 is then dissipated from the surface 44 of the cable jacket.

Figure 4:
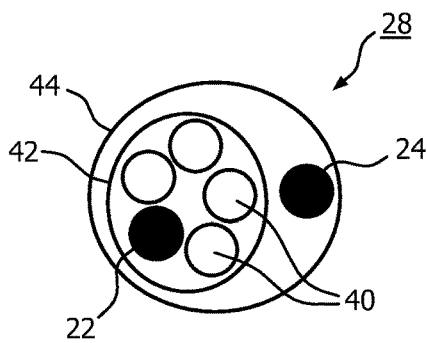

FIG. 4 illustrates another cable configuration in which the inbound (cool) conduit 22 is located in the cable braid 42 with the electrical conductor sub-bundles 40. The other conduit 24 is located outside the cable braid 42. The cable braid shields the conductors as in the previous example, and the sub-bundles again separate the two conduits. Alternatively the conduits can be reverse-packaged, with the outbound conduit 24 inside the cable braid 42 and the inbound conduit 22 located outside the braid. The electrical conductors, braid and conduits are again located in the cable jacket 44.

Figure 5:
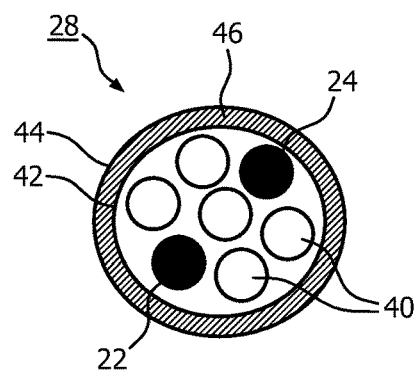

The implementation of FIG. 5 is similar to that of FIG. 3, with the addition of a thermally conductive layer 46 between the cable braid 42 and the outer surface 44 of the cable jacket. The thermally conductive layer, which may be be a part of the jacket, facilitates efficient heat transfer from the outbound (warm) conduit 24 to the surface of the cable 28.

Figure 6:
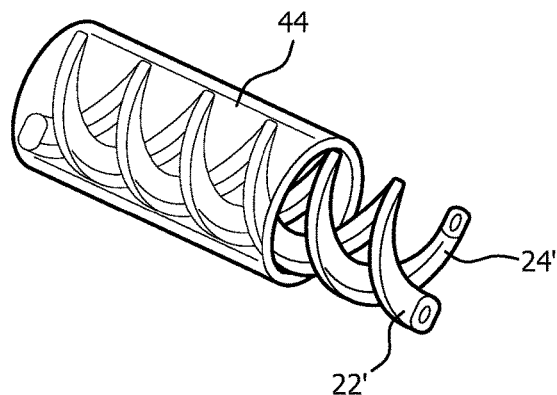

FIG. 6 illustrates another approach to separating the two fluid conduits, which is the use of helically wound tubes 22', 24' for the two conduits. The turns of the two helical windings are in interleaved alteration so that the two fluid conduits are always separated. The electrical conductors run through the center of the two helical tubes and the cable jacket 44 encases the helical conduits and conductors. A helically wound conduit presents a greater surface area to the cable jacket than does a straight conduit, affording greater heat transfer from the warmed fluid inside the conduit and cable.

Figure 7:
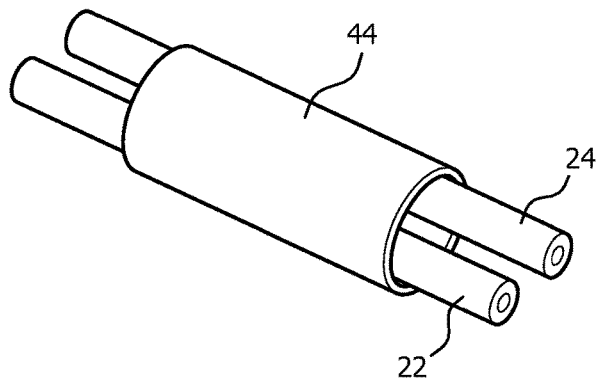
FIG. 7 illustrates a heat dissipating probe cable jacket with integrally formed fluid conduits in accordance with the principles of the present invention.

In the implementation of FIG. 7 the fluid conduits 22, 24 are formed integral with the cable jacket 44. The fluid conduits 22, 24 are thus formed during the extrusion of the cable jacket. The two fluid conduits will stay separated because they are integrally attached to opposite sides of the jacket, with the shielded electrical conductors running through the center of the jacket.

There are several ways to implement effective heat exchange between the thermally conductive backing block 165 and the heat exchanger 16 in the probe. One is to form the heat exchanger 16 as part of the spaceframe of the probe. The spaceframe is generally made of aluminum, which is an efficient conductor of heat. The heat exchanger 16 in FIG. 2 is then a cross-member of the spaceframe which mounts the acoustic stack and its thermally conductive backing block, with the backing block in thermal communication with the cross-member 16. A number of fluid channels are machined through the cross-member 16 and coupled to the fluid conduits so that incoming fluid from conduit 22 flows through the channels and out through the outbound conduit 24. As the cross-member 16 is heated by heat transferred to it by the backing block, that heat is carried away by the fluid flowing through the channels of the cross-member.

Another heat exchange implementation in the probe is to include a Peltier device in the heat exchanger 16, in thermal communication with the thermally conductive backing block 165. A Peltier device has a metal-to-metal junction of two types of metal. When an electrical current is applied to the junction, one side gets cool and the other side gets warm. With the cool side in thermal contact with the backing block, the Peltier device will then draw heat out of the backing block. A fluid tube, coil, or channel member of a heat exchanger as previously described, through which fluid of the fluid conduits 22, 24 flows, is in thermal communication with the warm side of the Peltier device and conducts and carries away heat from the warm side of the device through the fluid of the outbound conduit 24.

Figure 8:
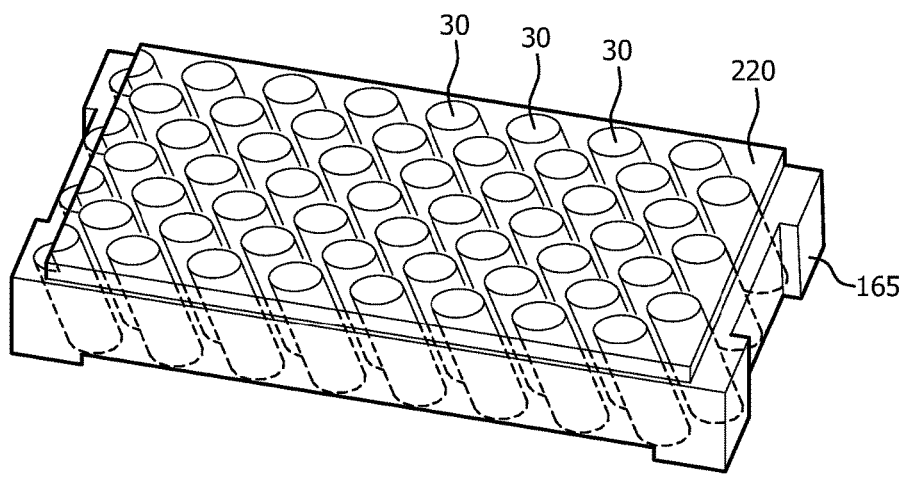
FIG. 8 is a perspective view of a thermally conductive backing block.
Figure 9:
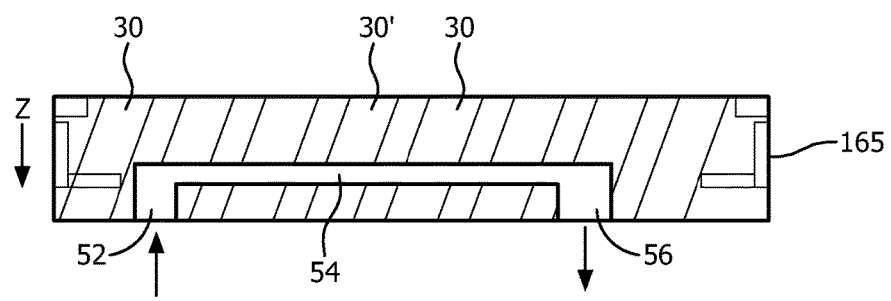
FIG. 9 illustrates a thermally conductive backing block with a fluid cooling channel in accordance with the principles of the present invention.
Figure 10:
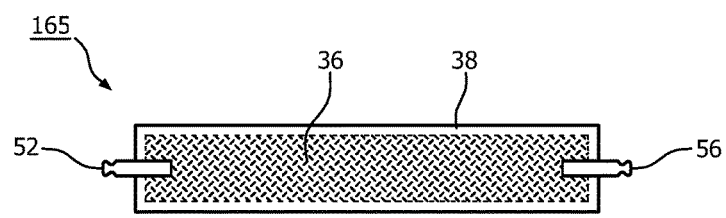
FIG. 10 illustrates a thermally conductive graphite foam backing block constructed in accordance with the principles of the present invention.

A third probe heat exchange implementation is shown in FIGS. 8, 9, and 10. In this implementation fluid heat exchange is done within the thermally conductive backing block. FIG. 8 illustrates a thermally conductive and acoustically attenuating graphite backing block as described in aforementioned U.S. patent application Ser. No. 61/453,690, filed Mar. 17, 2011. In this illustration the graphite is rendered translucent for clarity of illustration of the internal composite structure of the block. The acoustic dampening members are formed as a plurality of angled cylinders 30 of backing material in the backing block. The cylinders 30 are cut or drilled into the graphite block 20, then filled with acoustic dampening material such as epoxy filled with micro balloons or other acoustic damping particles. The tops of the cylinders 30 present a large area of acoustic dampening material to the back of the integrated circuit 160. A considerable amount of the undesired acoustic energy emanating from the back of the integrated circuit and acoustic stack will thus pass immediately into the dampening material. The angling of the cylinders as seen in FIG. 8 and the cross-sectional view of FIG. 9 assures that acoustic energy traveling in the Z-axis direction away from the ASIC will have to intersect dampening material at some point in the path of travel. Preferably, there is no path in the Z-axis direction formed entirely of graphite, and the angling of the cylinders does not promote reflection of energy back to the integrated circuit but provides scattering angles downward and away from the integrated circuit. In practice it may be sufficient to block most of the Z-axis pathways such as by blocking 95% of the pathways. Thus, the angling of the cylinders assures damping of all or substantially all of the Z-axis directed acoustic energy.

Heat, however, will find continuous pathways through the graphite between the cylinders 30. Since the flow of heat is from higher temperature regions to lower (greater thermal density to lesser), heat will flow away from the integrated circuit 160 and acoustic stack 100 to structures below the backing block 165 where it may be safely dissipated.

For fluid-based closed loop cooling a fluid channel 54 is formed in the backing block 165 as shown in the cross-sectional view of FIG. 9. The inbound (cooling) conduit 22 is coupled to the inlet port 52 of the fluid channel 54 and the outbound (warm) conduit 24 is coupled to the outlet port 56 of the fluid channel. As heat is transferred into the backing block 165 from ASIC 160, it is carried away from the backing block and probe by the fluid flow through the outbound fluid conduit 24. Heat exchange is done within the backing block itself with no separate heat exchanger.

Another implementation of this technique is shown in FIG. 10. In this implementation the thermally conductive and acoustically attenuating backing block 165 is formed of highly porous graphite foam 36. A coating of epoxy resin 38 on the outer surface of the graphite foam block provides structural rigidity and an epoxy surface that readily bonds to the ASIC 160. Holes are drilled through the epoxy layer on either side of the block and fluid ports 52 and 56 are located in the holes. The fluid ports thus access the highly porous interior of the block 165. The open structure of the porous graphite foam allows fluid to flow from one port to the other. Cool fluid flows in one port from the inbound conduit 22, through the porous foam structure, and out through the other port and into the outbound conduit 24. The graphite 36 efficiently conducts heat into the block 165 to be carried away by the fluid flow, the open foam structure promotes the fluid flow, and the graphite particles effectively scatter and attenuate acoustic energy from the back of the acoustic stack.

Figure 11:
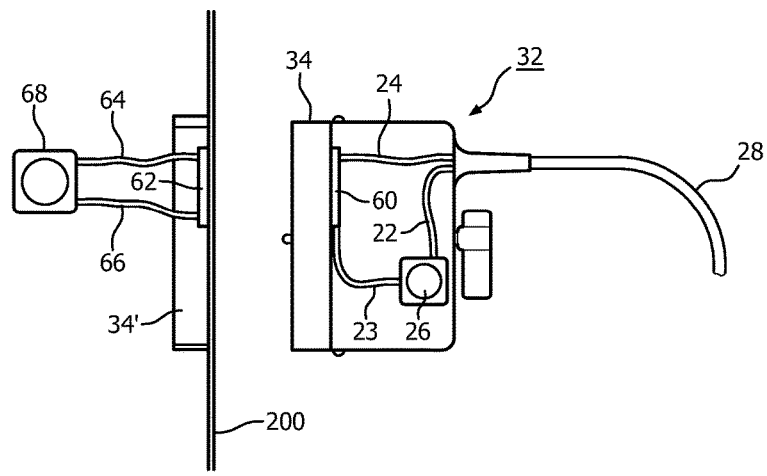
FIG. 11 illustrates an embodiment of the present invention in which heat is exchanged by metal-to-metal contact between a probe connector and a chiller in the mainframe ultrasound system.

If even greater heat dissipation is required than that afforded through the cable 28, additional cooling can be provided from the ultrasound system. Preferably, this additional cooling is provided without any fluid communication between the connector and the ultrasound system; it is desirable to keep the closed loop fluid flow completely within the probe, cable and connector. In FIG. 11 a metal plate 60 with fluid channels passing therethrough is located in the connector with the electrical socket 34. The outbound (warm) fluid conduit is coupled to one end of the fluid channels of plate 60, and a fluid conduit 23 is coupled from the other end of the fluid channels to the pump 26. Warm fluid will thus flow through the plate 60, heating the plate, before being pumped back to the cable and probe. When the probe connector 32 is plugged into the ultrasound system 200 and the electrical socket mates with the matching plug 34' of the ultrasound system, the plate 60 is pressed into contact against another fluid channel plate 62 of the ultrasound system. The plate 62 is cooled by apparatus in the ultrasound system. Since space and power is not at a premium in the ultrasound system as it is in the probe, a cooling system of almost any design can be used in the ultrasound system. A preferred cooling system is a chiller/evaporator 68, located in and powered by the ultrasound system, which pumps chilled fluid through fluid conduits 64, 66 and fluid channels of the plate 62. The plate 62 is thereby chilled to a considerably low temperature relative to ambient temperature. The metal to metal contact of chilled plate 62 and connector plate 60 which is warmed by fluid from the probe effects a rapid and efficient transfer of heat from the fluid in the warmed plate 60 to the chilled plate 62. The thermal communication between the two plates is established when the probe connector is plugged into the ultrasound system, and no fluid passes between the probe components and the ultrasound system.

Variations of the systems described above will readily occur to those skilled in the art. A heat exchanger need not be made of metal elements, but can use other conductive elements such as graphite, silicon, or other conductive materials. Obstruction of the fluid conduits due to bending, kinking, or twisting of the cable can be minimized by using redundant conduits, such as two inbound conduits alternated with two outbound conduits and located every 90° around the cable. Flow monitoring can be employed to assure the continued operation of the cooling system through the use of flow sensors, pressure sensors, or temperature monitoring. A fluid reservoir can be connected to the fluid loop to provide for expansion and contraction of the fluid due to temperature and pressure changes.

What is claimed is:

1. An ultrasonic transducer probe assembly comprising:
an acoustic stack comprising an array of transducer elements configured to transmit and receive ultrasound energy;
a thermally conductive backing block thermally and acoustically coupled to the acoustic stack and configured to reduce ultrasound energy received from the transducer elements, the thermally conductive backing block comprising a porous structure;
a probe connector configured to connect the transducer probe assembly to an ultrasound system;
a cable connected between a probe case and the probe connector; and
a fluid-based cooling system comprising:
a fluid loop extending through the cable from the probe case to the probe connector;
a pump, coupled to the fluid loop, which pumps fluid through the loop; and
a heat exchanger configured to transfer heat generated by the acoustic stack by dissipation of the heat outside the closed fluid loop, wherein the heat exchanger comprises a fluid channel that is coupled to the fluid loop and is configured to allow fluid to pass through the porous structure of the thermally conductive backing block.

2. The ultrasonic transducer probe assembly of claim 1, wherein the fluid loop comprises an inbound fluid conduit and an outbound fluid conduit coupled to the fluid channel of the thermally conductive backing block.

3. The ultrasonic transducer probe assembly of claim 2, further comprising first and second fluid ports that are coupled to the fluid channel of the thermally conductive backing block, wherein the inbound fluid conduit is coupled to the first fluid port and the outbound fluid conduit is coupled to the second fluid port.

4. The ultrasonic transducer probe assembly of claim 1, wherein the thermally conductive backing block comprises a material having a thermal conductivity substantially equivalent to that of graphite.

5. The ultrasonic transducer probe assembly of claim 4, wherein the thermally conductive backing block comprises a composite structure comprising a plurality of holes in the backing block comprising acoustic dampening material.

6. The ultrasonic transducer probe assembly of claim 5, wherein the holes further comprise a plurality of cylindrical holes extending from a top surface of the backing block to a bottom surface of the backing block, wherein the acoustic dampening material in the holes at the top surface comprise a majority of an area of the top surface.

7. The ultrasonic transducer array assembly of claim 6, wherein the holes are angled at a non-parallel angle with respect to a direction normal to a plane including the array of transducer elements.

8. The ultrasonic transducer array assembly of claim 7, wherein the holes are angled at an angle which causes acoustic energy traveling in the direction to be scattered away from the array of transducer elements.

9. The ultrasonic transducer array assembly of claim 1, wherein the thermally conductive backing block comprises graphite.

10. The ultrasonic transducer array assembly of claim 1, wherein the thermally conductive backing block comprises composite foam.

11. The ultrasonic transducer array assembly of claim 10, wherein the composite foam comprises a graphite foam.

12. The ultrasonic transducer array assembly of claim 11, wherein the composite foam backing block further comprises an exterior surface, and wherein the epoxy resin fills the porous structure of the foam backing block adjacent to the exterior surface.

13. The ultrasonic transducer array assembly of claim 1, further comprising an integrated circuit between the acoustic stack and the thermally conductive backing block.

14. The ultrasonic transducer array assembly of claim 13, wherein the integrated circuit comprises a beamformer application-specific integrated circuit (ASIC) coupled to a rearward side of the array of transducer elements.

15. The ultrasonic transducer array assembly of claim 14, wherein the thermally conductive backing block is bonded to the beamformer ASIC.

\* \* \* \* \*